United States Patent
Goetz et al.

(10) Patent No.: US 8,295,938 B2
(45) Date of Patent: Oct. 23, 2012

(54) PROGRAMMING A MEDICAL DEVICE WITH A GENERAL PURPOSE INSTRUMENT

(75) Inventors: Steven M. Goetz, North Oaks, MN (US); Touby A. Drew, Golden Valley, MN (US); Jeffrey T. Keacher, Stanford, CA (US)

(73) Assignee: Medtronic, Inc., Minneapolis, MN (US)

( * ) Notice: Subject to any disclaimer, the term of this patent is extended or adjusted under 35 U.S.C. 154(b) by 597 days.

(21) Appl. No.: 11/999,261

(22) Filed: Dec. 4, 2007

(65) Prior Publication Data

US 2008/0140157 A1  Jun. 12, 2008

Related U.S. Application Data

(60) Provisional application No. 60/873,187, filed on Dec. 6, 2006.

(51) Int. Cl.
*A61N 1/08* (2006.01)

(52) U.S. Cl. ............... 607/59; 607/60; 607/30; 607/31; 607/32

(58) Field of Classification Search .............. 607/59–60, 607/30–32
See application file for complete search history.

(56) References Cited

U.S. PATENT DOCUMENTS

| | | | |
|---|---|---|---|
| 4,365,633 A | 12/1982 | Loughman et al. | |
| 5,350,407 A | 9/1994 | McClure et al. | |
| 5,792,201 A | 8/1998 | Causey, III et al. | |
| 5,938,690 A | 8/1999 | Law et al. | |
| 6,178,503 B1 * | 1/2001 | Madden et al. | 713/2 |
| 6,249,703 B1 | 6/2001 | Stanton et al. | |
| 6,249,705 B1 * | 6/2001 | Snell | 607/59 |
| 6,250,309 B1 | 6/2001 | Krichen et al. | |
| 6,308,102 B1 | 10/2001 | Sieracki et al. | |
| 6,418,346 B1 | 7/2002 | Nelson et al. | |
| 6,442,433 B1 | 8/2002 | Linberg | |
| 6,480,745 B2 | 11/2002 | Nelson et al. | |
| 6,482,154 B1 | 11/2002 | Haubrich et al. | |
| 6,516,227 B1 | 2/2003 | Meadows et al. | |
| 6,574,511 B2 | 6/2003 | Lee | |
| 6,577,899 B2 | 6/2003 | Lebel et al. | |
| 6,599,250 B2 | 7/2003 | Webb et al. | |
| 6,609,032 B1 | 8/2003 | Woods et al. | |
| 6,622,048 B1 * | 9/2003 | Mann et al. | 607/46 |
| 6,659,968 B1 | 12/2003 | McClure | |

(Continued)

FOREIGN PATENT DOCUMENTS

EP  0 750 921 A2  1/1997

(Continued)

OTHER PUBLICATIONS

Microsoft, "Troubleshooting Windows 98 Startup Problems," May 7, 2007, Article ID: 188867, <http://support.microsoft.com/kb/188867>.*

(Continued)

*Primary Examiner* — Joseph Stoklosa

(74) *Attorney, Agent, or Firm* — Shumaker & Sieffert, PA

(57) ABSTRACT

An apparatus including a processor configured to selectively load a first operating system that controls general purpose computer functionality of the apparatus; and a second operating system different from the first operating system. The second operating system controls medical device programming functionality of the apparatus, enabling the apparatus to program a medical device including at least one implantable component.

45 Claims, 3 Drawing Sheets

U.S. PATENT DOCUMENTS

| | | | |
|---|---|---|---|
| 6,665,565 B1 | 12/2003 | Stomberg et al. | |
| 6,790,198 B1 | 9/2004 | White et al. | |
| 6,804,558 B2 | 10/2004 | Haller et al. | |
| 6,895,280 B2 | 5/2005 | Meadows et al. | |
| 6,978,181 B1 | 12/2005 | Snell | |
| 6,983,423 B2 | 1/2006 | Dvorak et al. | |
| 7,142,923 B2 | 11/2006 | North et al. | |
| 7,146,219 B2 | 12/2006 | North et al. | |
| 7,181,286 B2 | 2/2007 | North et al. | |
| 7,216,000 B2 | 5/2007 | North et al. | |
| 7,330,763 B1* | 2/2008 | Cullen et al. | 607/59 |
| 2002/0072358 A1 | 6/2002 | Schneider et al. | |
| 2002/0133207 A1 | 9/2002 | Thomas et al. | |
| 2003/0037172 A1 | 2/2003 | Lacombe et al. | |
| 2003/0130708 A1 | 7/2003 | Von Arx et al. | |
| 2003/0177031 A1 | 9/2003 | Malek | |
| 2004/0138518 A1 | 7/2004 | Rise et al. | |
| 2004/0138724 A1 | 7/2004 | Sieracki et al. | |
| 2004/0143302 A1 | 7/2004 | Sieracki et al. | |
| 2004/0167587 A1 | 8/2004 | Thompson | |
| 2004/0193884 A1 | 9/2004 | Molaro et al. | |
| 2004/0215286 A1 | 10/2004 | Stypulkowski | |
| 2006/0089684 A1 | 4/2006 | Blaha et al. | |
| 2006/0106433 A1* | 5/2006 | Mazar et al. | 607/60 |
| 2006/0212728 A1 | 9/2006 | Di Benedetto | |
| 2006/0241701 A1 | 10/2006 | Markowitz et al. | |
| 2006/0265020 A1 | 11/2006 | Fischell et al. | |

FOREIGN PATENT DOCUMENTS

| | | |
|---|---|---|
| EP | 0 753 327 A2 | 1/1997 |
| WO | WO 03/095024 A2 | 11/2003 |

OTHER PUBLICATIONS

Microsoft, "How to Manually Restore the Windows 98/Me Registry," May 7, 2007, Article ID: 221512, <http://support.microsoft.com/kb/221512>.*

Khalessi, A. A., Taylor, R. S., Brigham, D. D., North, R. B., "Automated, patient-interactive spinal cord stimulator adjustment: A cost-minimization analysis," Neurosurgery, 53:501-502, Aug. 2003.

North, R. B., Calkins, S. K., Campbell, D. S., Sieracki, J. M., Piantadosi, S. A., Daly, M. J., Dey, P. B., Barolat, G., "Automated, patient-interactive spinal cord stimulator adjustment: A randomized, controlled trial," Neurosurgery 52:572-580, Mar. 2003.

Fowler, K.R., "Neurological Stimulation System", Proceedings AAMI 21st Annual Meeting, Apr. 12-16, p. 27, 1986.

Fowler, K. R., North, R.B.: "Patient-interactive PC interface to implanted, multichannel stimulators," Proceedings of 39th Annual Conference on Engineering in Medicine and Biology, p. 380, 1986.

North, R.B., Fowler, K.R., "Computer-controlled, patient-interactive, multichannel, implanted neurological stimulators," Applied Neurophysiology, 50:39-41, 1987.

North, R.B., Nigrin, D.J., Szymanski, R.E., Fowler, K.R., "Computer-controlled, multichannel, implanted neurological stimulation system: Clinical assessment," Pain (Suppl.), 5:S83, 1990.

Fowler, K.R., North, R.B., "Computer-optimized neurological stimulation," Proc. Ann. Internat. Conf. IEEE Engineering Medicine and Biology Soc., 13:1692-1693, 1991.

Fowler, K.R., North, R.B., "Computer-optimized neurostimulation," APL Technical Digest, 12:192-197, 1991.

North, R.B., et al., "Spinal cord stimulation for chronic intractable pain: superiority of 'multi-channel' devices," Pain, V44, pp. 119-130, 1991.

North, R.B., Fowler, K.R., "Computer-controlled, patient-interactive neurological stimulation system," (Abstract) Acta Neurochir, 117:90, 1992.

North, R.B., Fowler, K.R., Nigrin, D.A., Szymanski, R.E., "Patient interactive, computer-controlled neurological stimulation system: Clinical efficacy in spinal cord stimulator adjustment," Journal of Neurosurgery, 76:967-972, 1992.

North, R.B., Fowler, K.R., Nigrin, D.A., Szymanski, R.E., Piantadosi, S., "Automated 'pain drawing' analysis by computer-controlled, patient-interactive neurological stimulation system," Pain, 50:51-57, 1992.

North, R.B., "Spinal Cord Stimulation for Chronic Intractable Pain," Electrical and Magnetic Stimulation of the Brain and Spinal Cord, pp. 289-301, 1993.

North, R.B., "The Role of Spinal Cord Stimulation in Contemporary Pain Management," APS Journal, vol. 2, No. 2, pp. 91-99, 1993.

North, R. B., Kidd, D. H., Zahurak, M., James, C. S., Long, D. M., "Spinal cord stimulation for chronic, intractable pain: Experience over two decades," Neurosurgery, 32:384-395, 1993.

North, R.B., Fowler, K.R., "Patient-interactive, microprocessor-controlled neurological stimulation system" (abstract), Stereotactic and Functional Neurosurgery, 62:309-315, 1994.

North, R. B., Levy, R. M., "Consensus conference on the neurosurgical management of pain," Neurosurgery, 34:756-761, 1994.

North, R. B., Kidd, D. H., Lee, M. S., Piantadosi, S., "A prospective, randomized study of spinal cord stimulation versus reoperation for the failed back surgery syndrom," Stereotactic and Functional Neurosurgery, 62:267-272, 1994.

North, R.B., et al., "Spinal Cord Stimulation for Chronic Pain," Functional Neurosurgery, vol. 6, No. 1, pp. 145-155, Jan. 1995.

North, R.B., Cutchis, P., "Spinal cord stimulation for chronic intractable pain," Spinal Cord Stimulation II, pp. 49-63, Darmstadt, Steinkopff, 1995.

North, R.B., McNamee, P., Wu, L., Piantadosi,S., "Artificial neural networks: Application to electrical stimulation of the human nervous system," (abstract) Stereotactic and Functional Neurosurgery, 65:161, 1995.

North, R. B., Kidd, D. H., Wimberly, R. L., Edwin, D., "Prognostic value of psychological testing in spinal cord stimulation patients: A prospective study," Neurosurgery, 39:301-311, 1996.

North, R. B., Kidd, D. H., Zahurak, M., Piantadosi, S., "Specificity of diagnostic nerve blocks: A prospective, randomized study of sciatica due to lumbosacral spine disease," Pain, 65:77-85, 1996.

North, R.B., McNamee, P., Wu,L., Piantadosi, S., "Artificial neural networks: Application to electrical stimulation of the human nervous system," Neurosurgical Focus, 2(1:1):1-5, 1997.

Alo, K. M. et al., "Computer Assisted and Patient Interactive Programming of Dual Octrode Spinal Cord Stimulation in the Treatment of Chronic Pain," Neuromodulation, vol. 1, No. 1, pp. 30-45, 1998.

North, R.B., Sieracki, J.N., Fowler, K.R., Alvarez, B., Cutchis, P.N., "Patient-interactive, microprocessor-controlled neurological stimulation system," Neuromodulation, 1(4):185-193, 1998.

U.S. Appl. No. 10/696,491, entitled "Body Region Indication", filed Oct. 29, 2003, Richard B. North, Jeffrey M. Sieracki.

U.S. Appl. No. 10/696,725, entitled "Failsafe Programming of Implantable Medical Devices", filed Oct. 29, 2003, Richard B. North, Jeffrey M. Sieracki.

Sieracki et al., U.S. Appl. No. 12/038,364 entitled "Failsafe Programming of Implantable Medical Devices", filed Feb. 27, 2008.

Keacher et al., U.S. Appl. No. 11/940,573 entitled "Medical Device Programming Safety," filed Nov. 15, 2007.

Keacher et al., U.S. Appl. No. 11/940,734 entitled "Telemetry Device for a Medical Device Programmer," filed Nov. 15, 2007.

Patent application entitled "Medical Device Programming Safety", U.S. Appl. No. 11/940,604, filed Nov. 15, 2007, Goetz et al.

Patent application entitled "Operating Environment Monitor for Medical Device Programming", U.S. Appl. No. 11/949,347, filed Dec. 3, 2007, Goetz et al.

Patent application entitled "Intelligent Discovery of Medical Device by a Programming System", U.S. Appl. No. 11/800,423, filed May 4, 2007, Goetz et al.

Request for Continued Examination Transmittal and Response to Final Office Action for U.S. Appl. No. 10/696,725, dated Oct. 15, 2007 (14 pgs.).

Advisory Action for U.S. Appl. No. 10/696,725, dated Sep. 27, 2007 (6 pgs.).

Response to Final Office Action for U.S. Appl. No. 10/696,725, dated Sep. 13, 2007 (15 pgs.).

Final Office Action for U.S. Appl. No. 10/696,725, dated Jul. 13, 2007 (8 pgs.).

Response to Office Action for U.S. Appl. No. 10/696,725, dated Apr. 4, 2007 (20 pgs.).

Office Action for U.S. Appl. No. 10/696,725, dated Dec. 5, 2006 (8 pgs.).

Response to Restriction Requirement for U.S. Appl. No. 10/696,725, dated Aug. 18, 2006 (12 pgs.).

Restriction Requirement for U.S. Appl. No. 10/696,725, dated Jul. 18, 2006 (6 pgs.).

"Comparison of virtual machines", last printed on Jan. 3, 2008, (14 pgs.) http://en.wikipedia.org/wiki/Comparison_of_virtual_machines.

"Microsoft SoftGrid® Microsoft Application Virtualization", last printed on Jan. 3, 2008, (3 pgs.) http://www.microsoft.com/systemcenter/softgrid/default.mspx.

Notification of Transmittal of the International Preliminary Report on Patentability for corresponding patent application No. PCT/US2007/024825, mailed Jan. 13, 2009, 5 pages.

Notification of Transmittal of the International Search Report and the Written Opinion of the International Searching Authority, or the Declaration, for corresponding patent application No. PCT/US2007/024825, mailed May 21, 2008, (11 pages).

Reply to Written Opinion for corresponding patent application No. PCT/US2007/024825, filed Oct. 1, 2008, (4 pages).

\* cited by examiner

PROGRAMMING A MEDICAL DEVICE WITH A GENERAL PURPOSE INSTRUMENT

This application claims the benefit of U.S. Provisional Application No. 60/873,187, filed Dec. 6, 2006, the entire content of which is incorporated herein by reference.

TECHNICAL FIELD

The invention relates to medical device programming and, more particularly, programming a medical device using a general purpose instrument such as, for example, a personal computer (PC).

BACKGROUND

Medical devices, such as implantable medical devices (IMDs), are used for monitoring and/or treatment of a wide variety of patient conditions. For example, medical devices are used as cardiac monitors or pacemakers, neurostimulators, or drug deliver devices. The operation of a medical device may be controlled or programmed by another device. In the case of an IMD, the device may be external to the patient.

Inappropriate programming of a medical device may pose a hazardous condition for the patient monitored or treated by the medical device. Traditionally, to ensure a high level of patient safety, instruments for programming, controlling, or otherwise interacting with medical devices have been run in heavily controlled environments, and deployed in a very limited range of configurations. These instruments utilize device-specific hardware and software operated by custom operating systems that are typically neither bootable by, nor capable of interacting with, the operating system in a general purpose computer system, such as a personal computer (PC).

SUMMARY

This lack of compatibility means that clinicians and patients must purchase, use and/or transport a separate instrument, i.e., programming device, to program and/or monitor a medical device. Further, development of the device-specific hardware and operating systems to control a medical device is a time consuming and expensive process, and the resulting software is less flexible and more limited in application than the operating systems in general purpose computers.

In general, the present disclosure is directed to techniques for allowing a general purpose computer, e.g., a PC, to run both an operating system controlling its general purpose functionality, e.g., word processing and Internet or other network access, and a medical device programming operating system that provides a platform for custom medical device programming software and thereby allows the computer to act as a programmer for the medical device. When executing the medical device programming operating system, the computer may act as, for example, a clinician programming device. The computer may selectively execute either operating system, or the medical device programming operating system may be a virtual operating system that executes over the general purpose operating system. The computer may boot the medical device programming operating system from an internal or external memory of the computer, or a peripheral medium. In some embodiments, the peripheral medium may be a medium within the medical device which is to be programmed, or another medical device with a dedicated, controlled computing environment, such as a dedicated patient therapy monitor (PTM), i.e., patient programmer.

In one embodiment, this disclosure is directed to an apparatus including a processor configured to selectively load a first operating system that controls general purpose computer functionality of the apparatus; and, a second operating system different from the first operating system, wherein the second operating system controls medical device programming functionality of the apparatus, enabling the apparatus to program a medical device including at least one implantable component.

In another embodiment, this disclosure is directed to a computer with a memory including a region formatted for a first operating system for controlling general purpose functionality of the computer, and a second operating system for controlling medical device programming functionality of the computer, enabling the computer to program a medical device, wherein the medical device includes at least one implantable component.

In yet another embodiment, this disclosure is directed to a system including a first medical device that includes at least one implantable component; and a personal computer including a processor that selectively boots and activates either a first operating system that provides general purpose functionality for the personal computer, or a second operating system, different from the first operating system, that provides medical device programming functionality for the personal computer to enable the personal computer to program the first medical device.

In yet another embodiment, this disclosure is directed to a method including selectively activating one or both of a first and second operating system in a computing device, wherein the first operating system provides general purpose functionality for the personal computer, and the second operating system provides medical device programming functionality for the personal computer; and programming a medical device comprising at least one implantable component when the second operating system is activated.

In yet another embodiment, the invention is directed to a computer-readable medium containing instructions. The instructions-cause a programmable processor to selectively activate one or both of a first and second operating system in a computing device, wherein the first operating system provides general purpose functionality for the personal computer, and the second operating system provides medical device programming functionality for the personal computer; and transmit programming instructions to a medical device including at least one implantable component when the second operating system is activated.

Embodiments of the invention may provide advantages. For example, provision of a medical device programming operating system on a general purpose computer may allow the general purpose computer to be used to program an implantable medical device, eliminating the necessity of a dedicated piece of computing hardware for this purpose. Further, actual or virtual separation of the operating systems on a general purpose computer may allow the medical device programming operating system to operate more safely than if it were to operate directly on the generally uncontrolled computing environment provided by a general purpose computer. Such separation may reduce the likelihood that resources critical for operation of the medical device programming operating system, or software running thereon, will be corrupted or otherwise altered by the general purpose operating system. Additionally, provision of a medical device programming operating system on a general purpose computer also makes possible the creation of dynamic and flexible medical device software that may be downloaded, accessed, used and updated in a way that is much more appropriate for clinicians and patients.

In certain applications the software may allow the clinician or patient to control the medical device with a general purpose instrument like a PC, which significantly reduces the amount and complexity of hardware required in a clinic environment. This hardware reduction may also allow personnel that travel with medical instruments, such as physicians and paramedics, field support, technicians, engineers, and salespersons, to combine a mobile work environment in a PC with the operating environment for programming a medical instrument. This reduces weight and complexity of hardware such a person is required to carry, and simplifies operation of the PC-controlled medical device in both standard and emergency treatment protocols. The software may also allow a single PC to control multiple medical devices or a number of different types of medical devices.

The details of one or more embodiments of the invention are set forth in the accompanying drawings and the description below. Other features, objects, and advantages of the invention will be apparent from the description and drawings, and from the claims.

DETAILED DESCRIPTION

Booting is a process for activating an operating system that starts when a user turns on a general purpose instrument, such as, for example, a PC. During booting the PC runs a boot sequence, which is a set of operations that load an operating system. The booting process begins when the CPU in the PC executes software, e.g., the basic input/output system (BIOS) of a PC, at a predefined address. The BIOS prepares the PC so other software programs stored on various media, such as hard drives, floppies, compact discs (CDs), uniform serial bus (USB) flash drives or other storage devices, can load, execute, and assume control of the PC.

The BIOS software contains rudimentary functionality to search for devices eligible to participate in booting. The BIOS typically evaluates a list, which may be preconfigured, configurable, or interactive, of devices until it finds one that is bootable. Suitable devices include, for example, local devices like hard disks, or peripheral/remote/removable devices such as, for example, media, USB connected peripherals including a Patient Therapy Manager (PTM) or telemetry head, and the like. If the BIOS finds a bootable device, it loads and executes a small program from a special section (most commonly the boot sector) of the software on the device. The boot process is considered complete when the operating system of the device is capable of running ordinary applications and the computer is ready to interact with the user.

Figure 1:
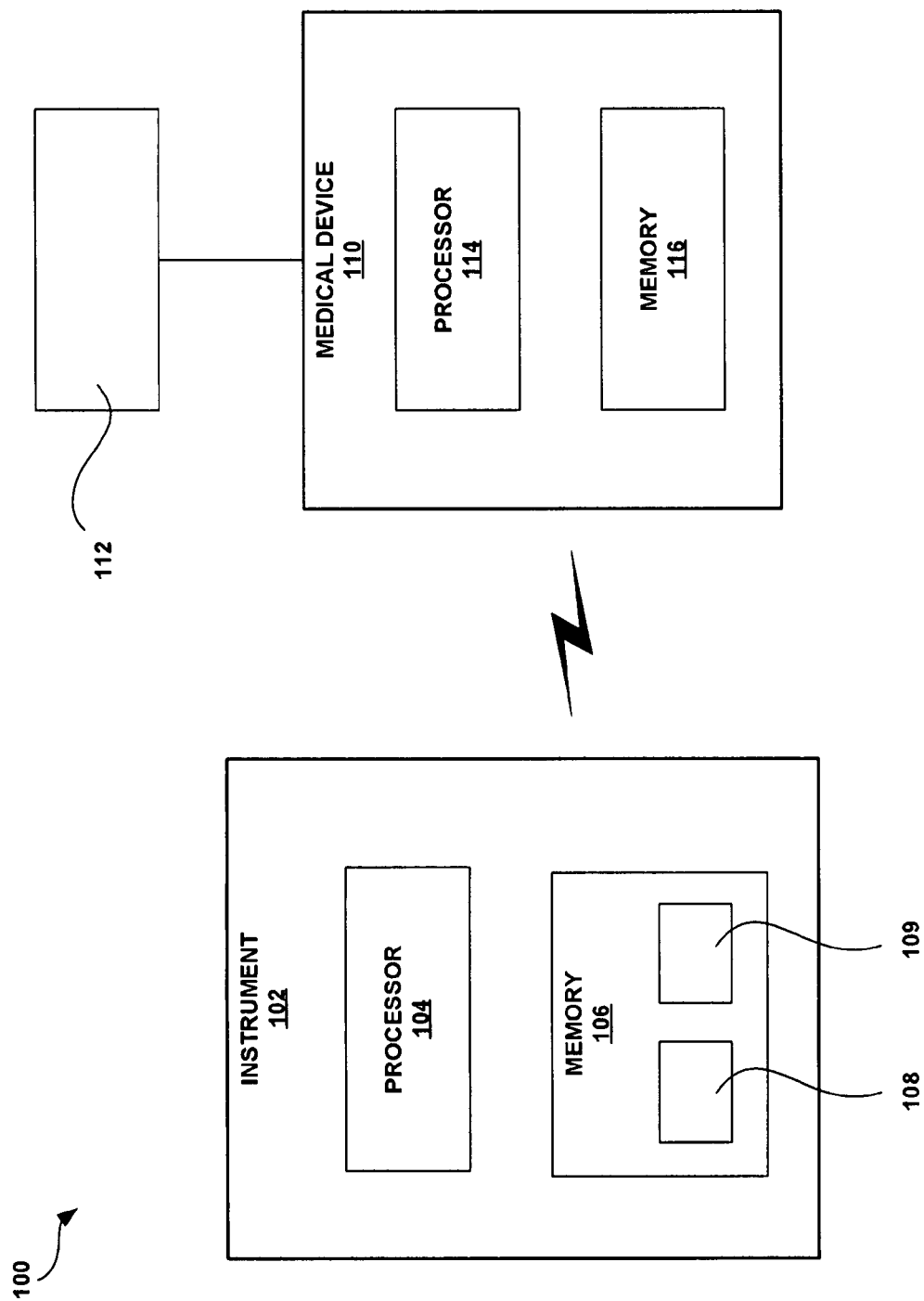
FIG. 1 is a block diagram illustrating a system including a general purpose instrument and a medical device with an implantable component.

FIG. 1 is a block diagram illustrating a system 100 including a general purpose instrument 102 and a medical device 110 with at least one implantable component 112. General purpose instrument 102 may be, for example, a personal computer (PC), and includes a processor 104. The processor 104 is configured to boot, i.e. load and activate, a first operating system 108. First operating system 108 controls the general purpose functionality of instrument 102, e.g., functionality associated with network access, web browsing, email, word processing, database access, or the like.

The general purpose instrument 102 is also configured to share data with, control or program the functionality of, or otherwise communicate with a medical device 110 that includes at least one implantable component 112. In some embodiments, the entire medical device 110 may be implanted in a patient. In example embodiments, implantable component may comprise a sensor, catheter, or lead comprising electrodes. Medical device 110 may comprise an implantable or external monitor, cardiac pacemaker, neurostimulator, or drug pump.

As illustrated in FIG. 1, implantable medical device may also include a processor 114 and memory 116. In some embodiments, processor 114 may control the operation of medical device 110, e.g., the delivery of therapy by the medical device, based on software and/or programmable values stored in memory 116. Furthermore, processor 114 may store data collected by the medical device during its operation in memory 116. For example, in embodiments in which medical device 110 monitors a patient, e.g., one or more physiological parameters, data gathered regarding the patient during such monitoring may be stored in memory 116. As examples, instrument 102 may communicate with medical device 110 and, more particularly, processor 104 may communicate with processor 114, for the purpose of modifying software or programmable values stored in memory 116, or retrieving gathered patient data stored in memory 116.

To facilitate communication with medical device 110, instrument 102 is also configured to boot up, i.e. load and activate, a second operating system 109. When second operating system 109 is active, instrument may run applications for communicating with, e.g., programming, medical device 110. Therefore, the processor 104 in the general purpose instrument 102 is capable of selectively booting both the first operating system 108 and the second operating system 109.

For example, if the instrument 102 is a PC, the preconfigured list of devices bootable by the PC BIOS may include media loaded with software specific to programming of the medical device 110. During the boot process, the software on the PC loads and activates the operating system 109 that facilitates programming of the medical device 110. Once the operating system 109 is booted and loaded by the PC, the processor 104 in the PC may operate in a second environment provided by the second operating system for programming the medical device, instead of or in addition to the first environment provided by its own operating system 108.

The processor 104 on the PC may be configured to determine the criteria required for accessing the second operating system 109. For example, additional authentication, training and restrictions may be required for using/booting the second operating system 109, and thereafter displaying data associated with the medical device 110, and utilizing, programming, or controlling the functionality of the medical device 110. An encrypted file scheme, access control, and/or additional integrity checks may optionally be used to limit access to and monitor the integrity of the operating environment for communicating with medical device 110. This may be important to protect patient data and privacy, as well as to ensure proper operation of medical device 110 during and after communication with, e.g., programming by, instrument 102.

Processor 104 and operating systems 108 and 109 may be configured to control, limit or maintain a desired level of separation and decoupling between the medical device programming environment and other environment(s) controlled by the PC, such as the general purpose computing environment provided by operating system 108. For example, the interaction between the operating systems and their associated environments with regard to use of data and access to memory 106, or portions thereof may be limited. In some embodiments, to provide a greater separation between the PC operating environment and the medical device programming environment, the second operating system 109 and the associated software for communicating with medical device 110 may be read only, e.g., stored in a portion of memory 106 or another memory that is configured to be read only. In such embodiments, if the operating system controlling or interacting with the medical device succumbs to malicious attack, viral infection, or is misused or unintentionally reconfigured, the processor 104 in the PC may be configured to perform an automatic or manual reboot to limit or remove the effects of malicious software on critical drivers and functionality of the second operating system.

Operating systems 108 and 109, the software used for booting operating systems 108 and 109, and the applications that run on operating systems 108 and 109 may be stored on any one or more memory devices of any combination of types. In the example illustrated by FIG. 1, operating systems 108 and 109, and the associated software, is stored in memory 106 within instrument 102, e.g., within the hard drive of the PC. In some embodiments, as discussed in greater detail below, one or more of operating system 109, the software used for booting operating system 109, and the applications run on operating system 109, are stored in a separate memory, which may be external to instrument 102, and accessible/readable by processor 104.

Figure 2:
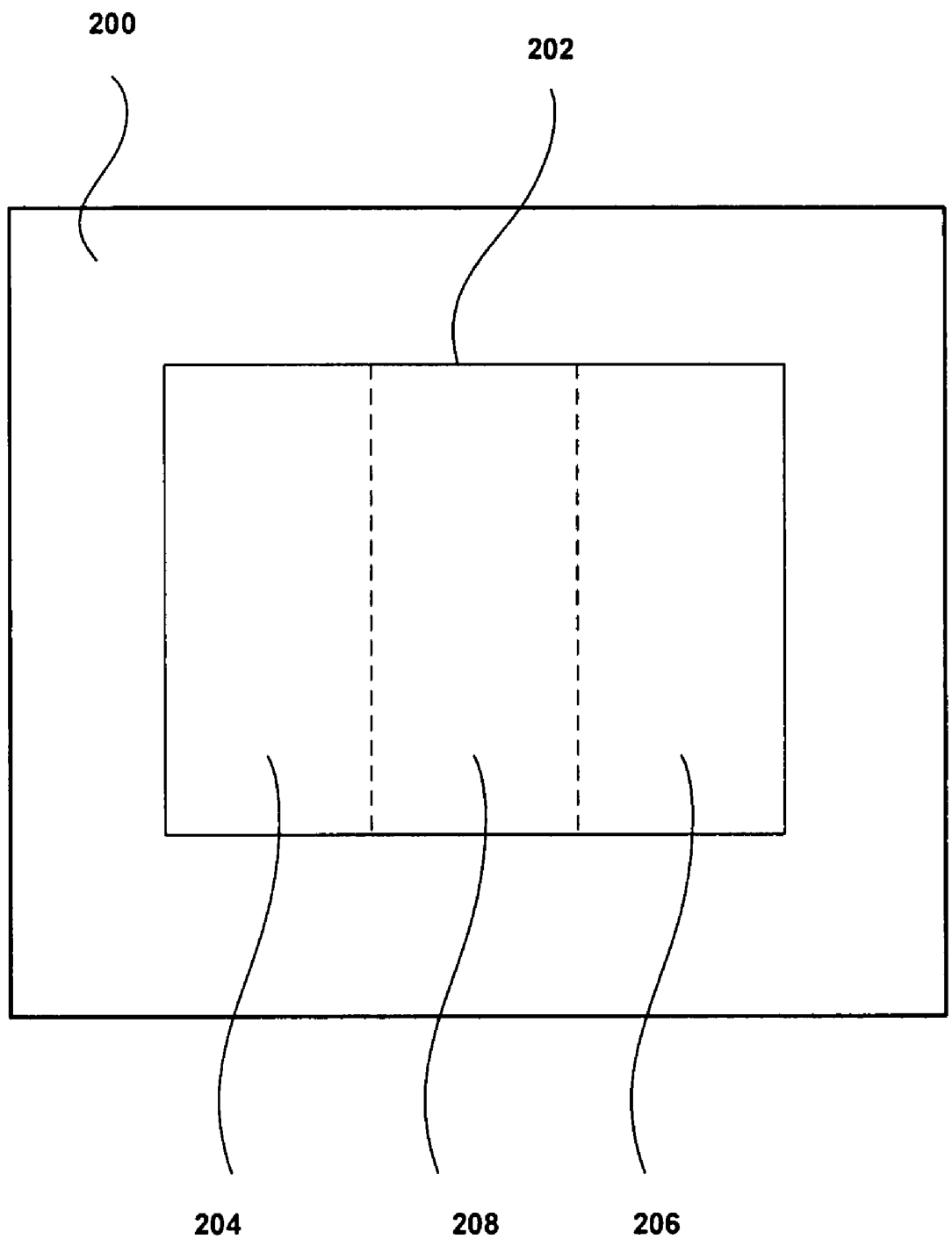
FIG. 2 is a block diagram illustrating a region in a memory of a general purpose instrument.

FIG. 2 is a block diagram illustrating a region 202 in a memory 200 of a general purpose computing instrument, e.g., PC. Memory 200 may correspond to memory 106 of instrument 102 described above with reference to FIG. 1. As illustrated in FIG. 2, region 202 of memory 200 may be partitioned and/or formatted for storage of a general purpose operating system and a medical device communication operating system, e.g., operating systems 108 and 109, respective boot software for such operating systems, respective software that executes on such operating systems, and respective data used by the software that executes on such operating systems. In other words, region 202 of memory 200 may be partitioned to separate and/or control access to data and functionality between the general purpose, e.g., PC, operating system and the medical device communication operating system.

For example, divisions may be created on one or more hard disks internal to the PC, which allow application of operating system-specific logical formatting. The selected region on the hard drive is then formatted for the appropriate operating system, and this formatting may be used to control interaction between the operating systems such as, for example, how files are copied from one operating system to another. For example, using this approach, during the boot process the PC BIOS or boot-loader checks a partition table for bootable partitions, and may under certain conditions boot a portion of the hard drive specifically formatted for the medical device communication operating system, e.g., operating system 106, or may access the remainder of the hard drive that is formatted for another operating system, e.g., general purpose or PC operating system 108.

For example, in one embodiment the secondary memory 200, e.g., hard disc, of the PC may be divided into an appropriate number of partitions such as, for example, a dual partition 204, 206. The dual partition forms in the first region of memory 204 a general use environment formatted for the PC operating system that is isolated from a second region of memory 206 with a medical device environment formatted for the medical device operating system. At boot time, the processor of the PC, e.g., processor 104, may be configured to select one of these environments and operating systems.

In some embodiments, the region 202 of the secondary memory of the PC may be formatted to include a shared partition 208. Shared partition 208 may be completely shared by the general purpose operating system and the operating system for interacting with the medical device, or the partition may be shared in a limited way such as, for example, for file transfer. For example, shared partition 208 can be formatted in such a way that the memory 200 is writable by only one of the operating systems, e.g., the medical device interaction operating system, and readable by both operating systems, or readable by both operating systems and writable by neither.

During the boot process, or at other times, the PC processor may be configured to check the contents of shared partition 208 for malicious or corrupted software. If such a problem is identified, the medical device interaction operating system, e.g., operating system 109, can modify or limit access to selected medical device data or functionality within shared partition 208.

During the boot process, or at other times, an encrypted file scheme may be used to limit or prevent access to portion 206 of the partition specific to the medical device operating system, which may be important to protect patient privacy or safety. Different or additional access criteria such as, for example, authentication, may be required to access portion 206 of the partition utilized by the medical device operating system 109. Different training or other restrictions may be required to limit access to specific portions of the partition occupied by the operating system for communicating with the medical device.

Separation between the general purpose environment and the medical device interaction environment may also be achieved by running a medical device virtual operating system on top of a general purpose operating system. Such a separation could be achieved with virtualization tools such as those described at http://en.wikipedia.org/wiki/Comparison_of_virtual_machines or on a more componentized basis, where for example a virtualization container may be built in/around/for each application or service such as described by http://www.softricity.com/index.html. For example, a virtualized general purpose operating system can be run at a low/lower/more-restricted priority on the operating system for interaction with the medical device, which would allow the general purpose operating system to continue to perform most functions, but with restricted interaction with the medical device interaction operating system. In another embodiment, a virtual medical device application environment can operate on top of the first general purpose operating system.

During operation of the medical device, the processor of the general purpose instrument, e.g., PC processor, may be configured to evaluate whether the instrument is running in the medical device interaction environment. If not, the operating system for interacting with the medical device may respond by any of, for example, refusing to run, reporting/logging the incident, or by invalidating license, warranty, certification, web addresses related to the medical device software, or computer network location associated with the software or PC. In the alternative, the general purpose instrument processor may reboot to into the correct environment and/or discourage reverse engineering, warn, present options, or apologize to the clinician or patient.

Figure 3:
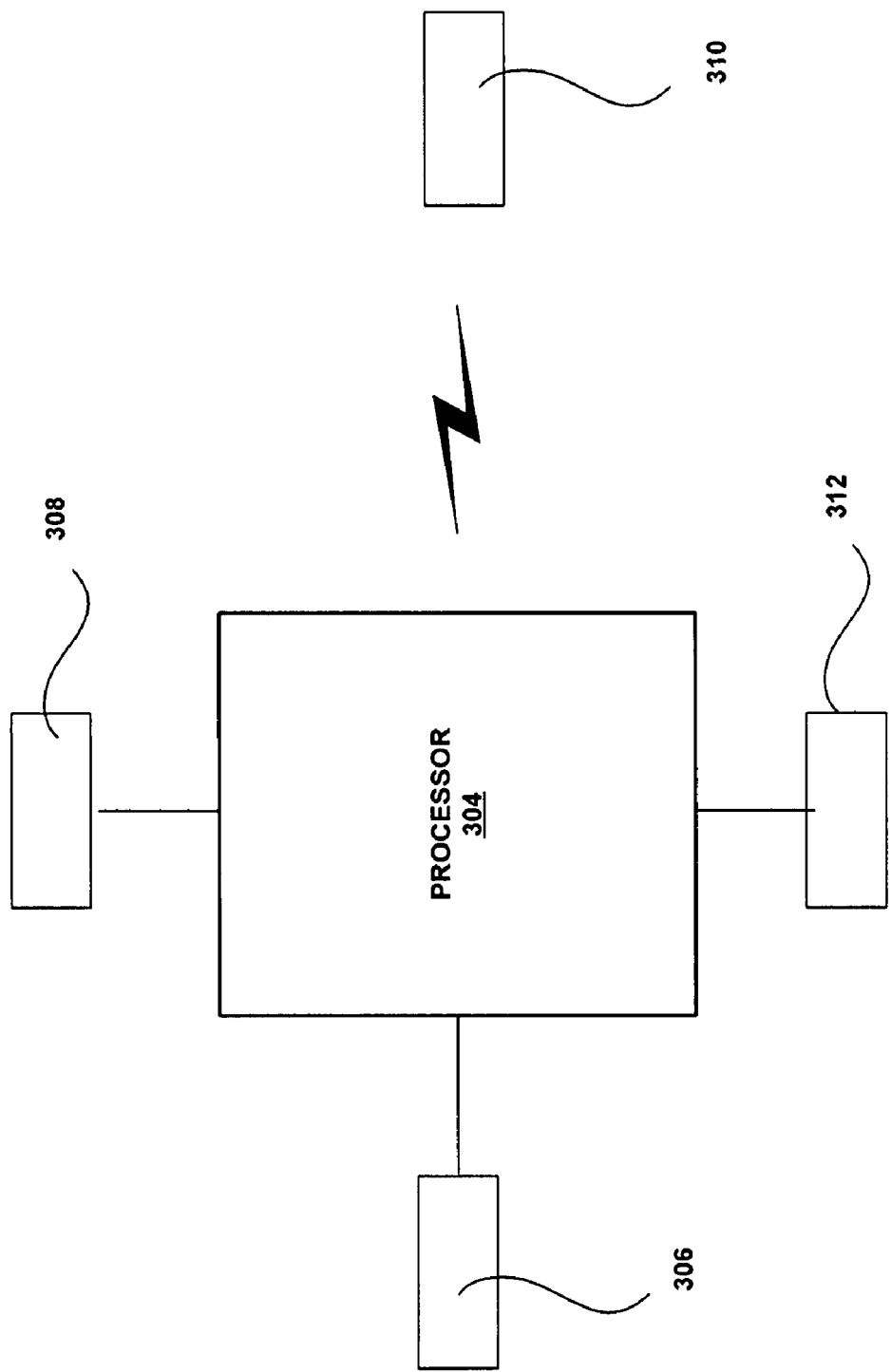
FIG. 3 is a block diagram illustrating media supply to a processor in a general purpose device.

FIG. 3 is a block diagram illustrating media supply to a processor 304 in a general purpose instrument. Processor 304 may correspond to processor 104 of general purpose instrument 102 of FIG. 1. The general purpose, e.g., PC, operating system and the medical device interaction operating system, as well as their respective associated boot and application software, are typically supplied to processor 304 via a memory device 306. Memory device 306 may include, for example, a hard disc in the general purpose instrument, or an external fixed (CD/DVD) or peripheral non-fixed (flash/peripheral) medium. Other suitable memory devices may include ROM, EEPROM, or other flash/hard disc components such as CDRW, DVDRW. The media may be fully or partially writable.

In some embodiments, processor 304 may boot the general purpose operating system and the medical device interaction operating system from different media. For example, processor 304 may boot the general purpose operating system from a memory, such as a hard disc, within the general purpose instrument. The medical device interaction operating system and/or associated boot software, by way of contrast, may be stored in an external or peripheral medium, e.g., CD/DVD or flash, which may act as a "boot disc" for the medical device interaction operating system. Processor 304 may also receive the application software that runs on the medical device interaction operating system from the peripheral/external medium.

In another embodiment, the medical device interaction operating system and/or associated boot software may be supplied to the processor 304 by a secondary processor controlled medical device 308 such as, for example, a Patient Therapy Manager (PTM), i.e., a Patient Programmer (PP), which may, unlike the PC or other general purpose instrument, comprise specialized hardware and software and be dedicated to programming a medical device. In the alternative, the instructions may be supplied by wireless communication, e.g., telemetry, from a device 310 such as, for example, a telemedicine base station, a telemetry head, a patient ID card, or an implantable or external medical device, e.g., medical device 110.

In another embodiment, to download the appropriate software and instructions to enable access to and interaction with the medical device interaction operating system, processor 304 can be connected to a memory device by any standard industry standard link such as USB, or by an industry supplied adapter. For example, such a link could be used to install the bootable software and properly configure the processor on a clinician PC. This software and/or that on a secondary controlled medical device, such as the PTM, could further validate (automatically or with further user input) the medical device environment and enable the PC or other general purpose instrument to access the medical device operating system. The secondary controlled medical device such as the PTM could also serve as a proxy between the PC operating environment and the medical device interaction environment, which may enable simple interactions such as initializing or installing files, or more sophisticated capabilities such as updating, monitoring or management.

In another embodiment, the medical device interaction operating system and/or associated boot software may be downloaded by input from a memory device 312 associated with a patient in which the implantable component 112 (FIG. 1) is inserted. The software and instructions may be downloaded into the PTM or PP and/or to another general purpose device (such as a PC) for later transfer or archiving. The patient or clinician could also obtain the software (or a link to acquire it) by regular mail, by email, via a server-client system, from a polling scheme, or from a subscription based service.

Various embodiments of the invention have been described. These and other embodiments are within the scope of the following claims.

The invention claimed is:

1. An apparatus comprising:
    a memory comprising:
        a first operating system that controls general purpose computer functionality of the apparatus; and
        a second operating system different from the first operating system, wherein the second operating system controls medical device programming functionality of the apparatus, enabling the apparatus to program a first medical device comprising at least one implantable component; and
    a processor configured to:
        selectively load and activate either the first operating system or the second operating system;
        receive instructions from a second medical device different from the first medical device; and
        load and activate the second operating system in response to the instructions received from the second medical device.

2. The apparatus of claim 1, wherein the processor is further configured to apply a first set of criteria for accessing the first operating system and a second set of criteria for accessing the second operating system.

3. The apparatus of claim 2, wherein the second criteria comprises at least one of an encrypted file scheme, or an authentication procedure different from an authentication procedure in the first criteria.

4. The apparatus of claim 1, wherein the processor is configured to format the memory to provide a region formatted for the first and the second operating systems, and wherein the first operating system and the second operating system share the formatted region to form a shared partition.

5. The apparatus of claim 4, wherein the shared partition is formatted such that the memory is readable by both the first and the second operating systems, and writable by only the second operating system.

6. The apparatus of claim 4, wherein the shared partition is formatted such that the memory is readable by both the first and the second operating systems, and writable by neither the first nor the second operating systems.

7. The apparatus of claim 1, wherein the processor is configured to format the memory to provide a first memory region formatted for the first operating system and a second memory region formatted for the second operating system, and the first region is different from the second region.

8. The apparatus of claim 7, wherein an encrypted file scheme limits access to the first memory region formatted for the first operating system and the second memory region formatted for the second operating system, and the first region is different from the second region.

9. The apparatus of claim 7, wherein the processor limits access to the first memory region formatted for the first operating system and the second memory region formatted for the second operating system, and the first region is different from the second region.

10. The apparatus of claim 1, wherein the processor is configured to load both of the first and second operating systems from the memory.

11. The apparatus of claim 1, wherein the memory comprises an internal memory and an external memory, and wherein the processor is configured to load the first operating system from the internal memory and the second operating system from the external memory.

12. The apparatus of claim 1, wherein the second operating system comprises a virtual operating system that runs on top of the first operating system.

13. The apparatus of claim 1, wherein the apparatus comprises a general purpose personal computer.

14. The apparatus of claim 1, wherein the processor is configured to detect data corruption in the memory and limit access to the second operating system when data corruption is detected in the memory.

15. The apparatus of claim 1, wherein the processor is configured to load and activate the second operating system based on instructions supplied by the first medical device.

16. The apparatus of claim 1, wherein the processor is configured to receive the second operating system from the second medical device.

17. The apparatus of claim 1, wherein the second medical device is a patient therapy manager (PTM).

18. A computer comprising:
a memory comprising:
a first operating system for controlling general purpose functionality of the computer; and
a second operating system for controlling medical device programming functionality of the computer, enabling the computer to program a first medical device, wherein the first medical device comprises at least one implantable component; and
a processor configured to:
selectively boot and activate either the first operating system or the second operating system;
receive instructions from a second medical device different from the first medical device; and
boot and activate the second operating system in response to the instructions received from the second medical device.

19. The computer of claim 18, wherein the memory comprises a first region and a second region, wherein the first region is formatted for the first operating system and the second region is formatted for the second operating system.

20. A system comprising:
a first medical device that includes at least one implantable component; and
a personal computer comprising a processor that selectively boots and activates either a first operating system that provides general purpose functionality for the personal computer, or a second operating system, different from the first operating system, that provides medical device programming functionality for the personal computer to enable the personal computer to program the first medical device, wherein the processor is configured to receive instructions from a second medical device different from the first medical device, and wherein the processor is configured to boot and activate the second operating system in response to the instructions received from the second medical device.

21. The system of claim 20, wherein the processor boots and activates the second operating system from at least one of an external fixed or a peripheral non-fixed medium.

22. The system of claim 21, wherein the fixed medium is selected from the group consisting of a compact disc (CD) and a digital versatile disc (DVD).

23. The system of claim 21, wherein the non-fixed medium comprises a flash media device.

24. The system of claim 20, wherein the second medical device is a patient therapy manager (PTM).

25. The system of claim 20, wherein the second medical device includes at least one of a telemetry head and a patient ID card.

26. The system of claim 20, wherein the processor boots and activates the second operating system based on instructions supplied by the first medical device.

27. The system of claim 20, wherein the processor is configured to detect data corruption in the second operating system and limit access to the second operating system when data corruption is detected in the second operating system.

28. The computer of claim 18, wherein the processor is configured to receive the second operating system from the second medical device.

29. The computer of claim 18, wherein the second medical device is a patient therapy manager (PTM).

30. The system of claim 20, wherein the processor is configured to receive the second operating system from the second medical device.

31. A method comprising:
selectively booting and activating a first operating system or a second operating system in a computing device, wherein the first operating system provides general purpose functionality for the computing device, and the second operating system provides medical device programming functionality for the computing device; and
programming a first medical device comprising at least one implantable component when the second operating system is activated, wherein booting and activating the second operating system comprises receiving instructions from a second medical device different from the first medical device, and wherein booting and activating the second operating system further comprises booting and activating the second operating system in response to the instructions received from the second medical device.

32. The method of claim 31, further comprising:
applying a first set of criteria for accessing the first operating system; and
applying a second set of criteria for accessing the second operating system.

33. The method of claim 32, wherein applying a second set of criteria comprises applying at least one of an encrypted file scheme, or an authentication procedure different from an authentication procedure in the first criteria.

34. The method of claim 31, wherein the computing device comprises a memory, the method further comprising loading both of the first and second operating systems from the memory.

35. The method of claim 31, wherein the computing device comprises a memory, the method further comprising loading the first operating system from the memory and the second operating system from another memory external to the computing device.

36. The method of claim 35, wherein loading the second operating system from another memory external to the computing device comprises loading the second operating system from at least one of an external fixed or a peripheral non-fixed medium.

37. The method of claim 35, wherein loading the second operating system from another memory external to the computing device comprises loading the second operating system from the second medical device.

38. The method of claim 31, wherein the second medical device includes at least one of a telemetry head and a patient ID card.

39. The method of claim 35, wherein loading the second operating system from another memory external to the computing device comprises loading the second operating system from the first medical device.

40. The method of claim 31, further comprising running the second operating system as a virtual operating system on top of the first operating system.

41. The method of claim 31, further comprising:
   detecting data corruption in the second operating system; and
   limiting access to the second operating system when data corruption is detected in the second operating system.

42. The method of claim 31, further comprising receiving the second operating system from the second medical device.

43. A computer-readable storage medium comprising instructions that cause a programmable processor to:
   selectively boot and activate either a first operating system or a second operating system in a computing device, wherein the first operating system provides general purpose functionality for the computing device, and the second operating system provides medical device programming functionality for the computing device; and
   transmit programming instructions to a first medical device comprising at least one implantable component when the second operating system is activated, wherein booting and activating the second operating system comprises receiving instructions from a second medical device different from the first medical device, and wherein booting and activating the second operating system further comprises booting and activating the second operating system in response to the instructions received from the second medical device.

44. The computer-readable storage medium of claim 43, further comprising instructions that cause a programmable processor to:
   apply a first set of criteria for accessing the first operating system; and
   apply a second set of criteria for accessing the second operating system.

45. The computer-readable storage medium of claim 43, further comprising instructions that cause the programmable processor to:
   detect data corruption in the second operating system; and
   limit access to the second operating system when data corruption is detected in the second operating system.

* * * * *